United States Patent [19]

Sibley et al.

[11] Patent Number: 4,649,711

[45] Date of Patent: Mar. 17, 1987

[54] APPARATUS AND METHOD FOR INFRARED OPTICAL ELECTRONIC QUALITATIVE ANALYSIS OF A FLUID INDEPENDENT OF THE TEMPERATURE THEREOF

[75] Inventors: Howard W. Sibley, Baldwinsville, N.Y.; Karl Shaffer, Bridgeville, Pa.

[73] Assignee: Carrier Corporation, Syracuse, N.Y.

[21] Appl. No.: 771,911

[22] Filed: Sep. 3, 1985

[51] Int. Cl.$^4$ .................... G01K 13/00; G01N 33/28
[52] U.S. Cl. .................................... 62/129; 340/631; 356/70; 356/442; 250/301; 250/343
[58] Field of Search ............... 62/126, 129; 250/343, 250/346, 351, 344, 205, 301, 373, 574, 354.1; 356/433, 436, 440, 338, 442, 70; 340/631

[56] References Cited

U.S. PATENT DOCUMENTS

| | | | |
|---|---|---|---|
| 3,736,431 | 5/1973 | Childs | 356/442 X |
| 4,124,301 | 11/1978 | Pocock | 356/442 X |
| 4,466,076 | 8/1984 | Rosenthal | 364/571 |
| 4,480,190 | 10/1984 | Burough et al. | 250/343 |
| 4,490,612 | 12/1984 | Tormala | 250/339 |
| 4,490,988 | 1/1985 | Vogel et al. | 340/631 X |

*Primary Examiner*—Harry Tanner
*Attorney, Agent, or Firm*—Robert H. Kelly

[57] ABSTRACT

An apparatus and method is provided for infrared qualitative analysis of a fluid independent of the temperature of the fluid. A first signal is generated in response to detected infrared energy passing through the fluid, and a second datum signal is provided for comparison with the first signal, wherein the second signal indicates a non-radiating state. The energy difference between the two signals is provided to a microprocessor control system for computing the fluid quality as a function of the energy difference independent of the temperature of the fluid.

22 Claims, 4 Drawing Figures

APPARATUS AND METHOD FOR INFRARED OPTICAL ELECTRONIC QUALITATIVE ANALYSIS OF A FLUID INDEPENDENT OF THE TEMPERATURE THEREOF

BACKGROUND OF THE INVENTION

The present invention pertains to infrared analysis of matter, and more particularly to infrared optical electronic qualitative analysis of a fluid independent of the temperature thereof.

Although the present invention is applicable to qualitative analysis of any type of fluid independent of its temperature, it will be described hereafter specifically in regard to refrigeration, air conditioning, or similar systems using a machine, such as a compressor, requiring a lubricant, such as a petroleum-based oil. For example, in an air conditioning system including a condenser, an evaporator, and a compressor, some type of lubrication is used during operation of the compressor. During the normal course of use, the lubricant will become contaminated as a result of its own decomposition or with water, acid, or other particulates from different parts or areas of the system. Eventually, the lubricant will need to be drained and replaced by new lubricant to maintain efficient operation of the compressor and the system.

Currently, a conventional method of monitoring lubricant quality of a compressor, such as a centrifugal compressor, requires obtaining a sample of the lubricant and sending it to a laboratory for analysis. Generally, this includes a long period of delay in receiving the determined contamination level, and if the results indicate the lubricant is in satisfactory condition, a needless expense has been incurred. Furthermore, the degradation of lubricant may result from a series of occurrences during operation that may not be reflected in the static oil analysis. Therefore, an in situ evaluation or analysis would have the advantage of sensing these impulse occurrences. For example, a momentary leak could inject water into the system at one point in time, and might not be detected by a static oil sample.

An accurate determination of lubricant quality via optical electronics should include correction or compensation for temperature variations within the fluid during operation of the system. One such known method of correcting for temperature variations includes the use of temperature sensing devices, such as thermistors, to detect either one or several temperatures at different points, and then to feed the readings to a control system that would compensate for temperature changes.

SUMMARY OF THE INVENTION

It is an object of the present invention to provide an apparatus and method for infrared optical electronic qualitative analysis of a fluid independent of the temperature thereof.

Another object of the present invention is to provide an apparatus and method for infrared optical electronic qualitative analysis of a lubricant without having to withdraw a sample of the lubricant from its operating environment.

Yet another object of the present invention is to provide an apparatus and method for the infrared optical electronic qualitative analysis of a fluid wherein a voltage differential is utilized to minimize and compensate for temperature variations.

A further object of the present invention is to provide an apparatus for infrared optical electronic qualitative analysis of a fluid independent of the temperature thereof which is compact in size and relatively inexpensive to operate.

In one form of the invention, there is provided an apparatus for infrared qualitative analysis of a fluid independent of the temperature of the fluid, the apparatus comprising a passage substantially transparent to infrared energy for delivering a flow of the fluid therethrough, an infrared device for radiating infrared energy through the passage, a detection device for detecting infrared energy radiated through the passage and for generating an infrared-responsive signal indicative of the detected infrared energy and a datum signal indicative of a non-radiating energy state of the infrared device, and a microprocessor control means for receiving and measuring an energy difference between the two signals and computing from the energy difference the quality of the fluid independent of its temperature.

In another form of the present invention, there is provided a method for infrared qualitative analysis of a fluid independent of the temperature of the fluid, comprising the steps of providing fluid to be analyzed, radiating infrared energy through the fluid, detecting the infrared energy radiated through the fluid, generating an infrared-responsive signal indicative of the detected infrared energy, generating a datum signal indicative of a non-radiating infrared energy state, determining the energy difference between the signals, and computing from the determined energy difference the quality of the fluid independent of its temperature.

BRIEF DESCRIPTION OF THE DRAWINGS

The above-mentioned and other features and objects of this invention, and the manner of attaining them, will become more apparent and the invention itself will be better understood by reference to the following description of an embodiment of the invention taken in conjunction with the accompanying drawings, wherein.

DESCRIPTION OF A PREFERRED EMBODIMENT

The apparatus and method of the present invention qualitatively analyzes the total cumulative effect of contaminants on a fluid and does so independent of any temperature changes under which the fluid may undergo. The analysis of the fluid independent of its temperature is accomplished by means of infrared irradiation of the fluid and determining a voltage difference between the detected radiation passing through the fluid and a datum voltage during a non-irradiation state.

In a specific embodiment of the present invention, it is contemplated for use in a refrigeration, air conditioning, or similar system utilizing a fluid, such as a fluorocarbon refrigerant, for temperature conditioning purposes. The refrigerant can also be any fluid that has similar infrared characteristics of a fluorocarbon refrigerant, as further described below.

In any system requiring lubrication, such as the compressor in a refrigeration system, the lubricant tends to become contaminated and require replacement. In a refrigeration or similar system, the lubricant can become contaminated due to its normal chemical breakdown over continued use, or with water, acid, and other particulate matter within the refrigeration system. As indicated earlier, the present invention indicates a total cumulative effect of all contaminants including foaming lubricant during compressor startup.

A correlation exists between lubricant degradation and infrared energy transmittance through the lubricant. A preferred infrared bandwidth for use with a petroleum-based lubricant having an amount of a fluorocarbon refrigerant mixed therewith is preferably in a range of about seven to fourteen (7-14) microns. An optimum range is about 9.75 to 10.25 microns. As indicated above, the lubricant can be mixed with any fluid having the infrared characteristics of a fluorocarbon refrigerant such that there is at least 75% transmission in the 9.75 to 10.25 range.

Figure 1:
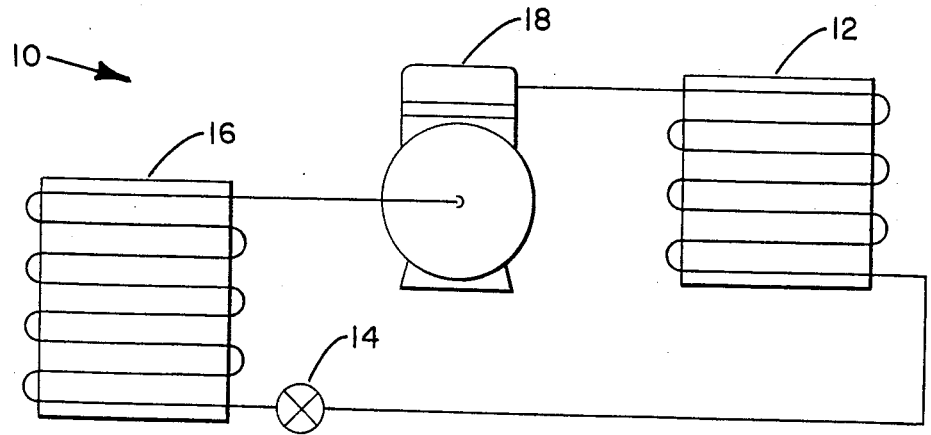
FIG. 1 is a schematic of a refrigeration system in which an embodiment of the present invention can be incorporated.

Referring now to FIG. 1, there is illustrated a refrigeration system 10 comprising condenser 12, expansion valve 14, evaporator 16, and a compressor 18 including a lubrication system therefor.

Figure 2:
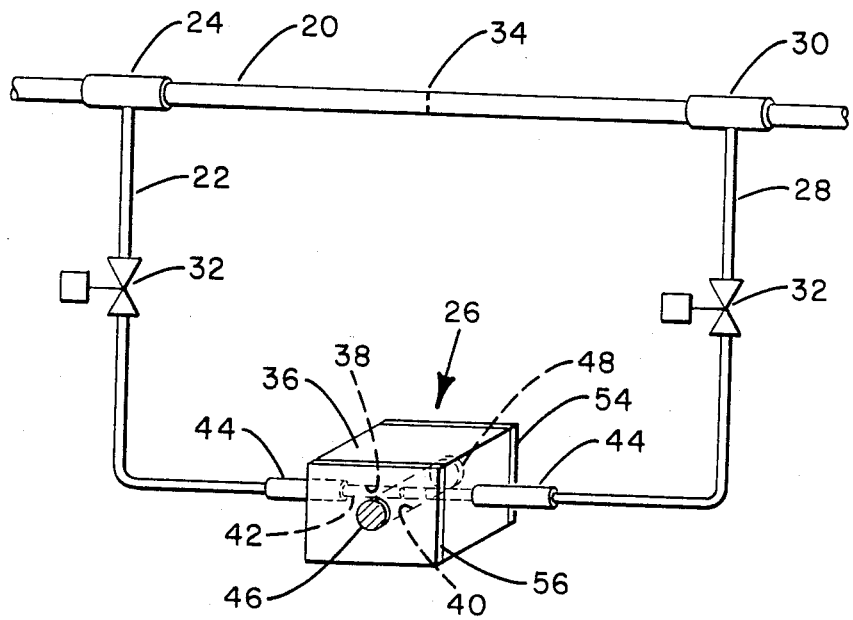
FIG. 2 is a schematic of one embodiment of the present invention.

FIG. 2 is a schematic of one embodiment of the present invention incorporated with a lubricant line 20, which is part of the total lubricant system (not shown) for compressor 18. A branch line 22 is coupled to lubricant line 20, such as by a suitable connector 24, for delivering a flow of lubricant through infrared analyzer 26 of the present invention. A second branch line 28 directs the lubricant from analyzer 26 back to lubricant line 20 by means of connector 30. Both branch lines 22, 28 include respective solenoid control valves 32 for opening or closing their respective lines. Lubricant line 20 has a flow restrictor 34 between branch lines 22, 28 for balancing the pressure drop thereacross, thereby allowing a portion of the lubricant to flow through lines 22, 28.

Figure 3:
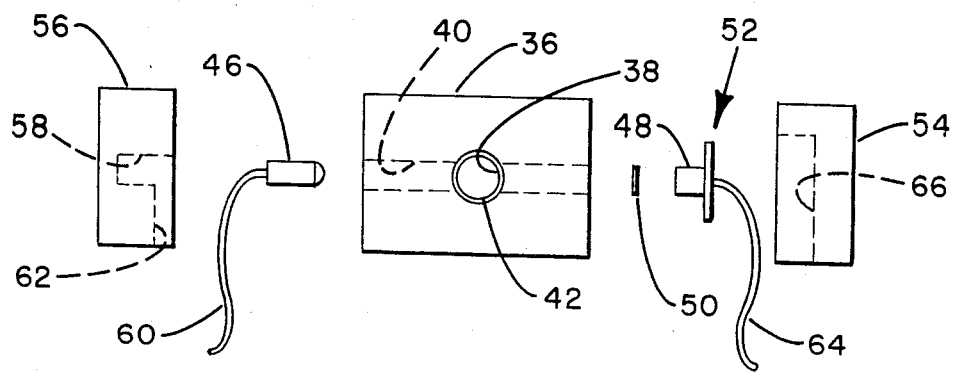
FIG. 3 is an exploded view of the embodiment in FIG. 2.

Referring now to FIGS. 2 and 3, infrared analyzer 26, as one embodiment of the present invention, comprises a main body 36 having intersecting passages 38, 40 therein. Main body 36 is made of a material having low emissivity, such as acetal plastic, which does not readily absorb infrared energy. Passage 38 houses a tube 42 made of a material with good mid-range infrared transmission such as polyethylene and is coupled to branch lines 22, 28 by means of connectors 44. Thus, the flow of lubricant is directed through branch line 22, connector 44, polyethylene tube 42, connector 44, and then to branch line 28.

At one end of passage 40 is an infrared source 46 for transmitting infrared energy through passage 40, tube 42 and the lubricant flowing therethrough, to the opposite end of passage 40. Infrared source 46 must have suitable infrared emission characteristics for emitting infrared energy, such as special incandescent lamps with fast rise-fall illuminance. In the opposite end of passage 40 there is disposed an infrared detector 48 for detecting infrared energy passing through passage 40. A filter 50 is placed in front of detector 48 for permitting only selected bandwidths of IR energy to pass therethrough. The selected bandwidth could be the preferred bandwidth of about 7-14 microns or the optimum bandwidth of about 9.75-10.25 microns. Detector 48 is preferably a pyroelectric detector such as lithium tantalate and filter 50 can be a germanium filter. Further, filter 50 could be disposed between IR source 46 and tube 42, rather than between tube 42 and detector 48. If necessary, filter 50 could be dispensed with, but IR source 46 would be required to emit infrared energy only within a selected band width.

Figure 4:
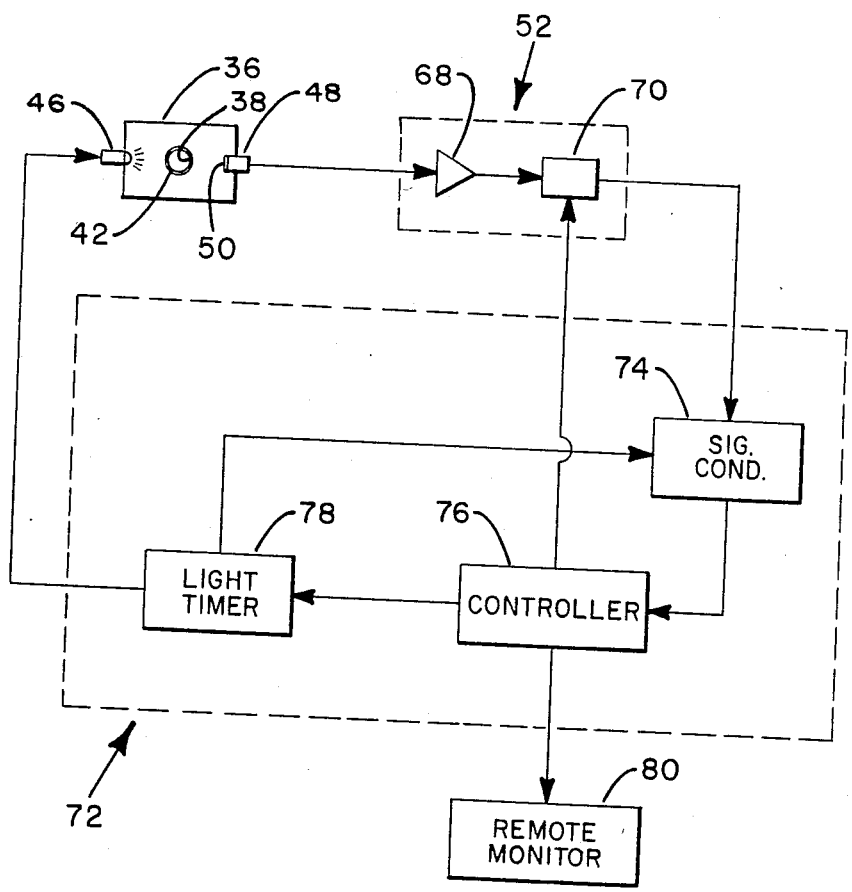
FIG. 4 is a schematic block diagram of the embodiment in FIG. 2.

Referring additionally to FIG. 4, detector 48 is mounted on printed circuit board 52, and the combination of filter 50, detector 48, and board 52 is secured to main body 36 by an end cap 54. A second end cap 56 secures infrared source 46 to main body 36. Both caps 56 are made of a material having low emissivity. As illustrated in FIG. 3, IR source 46 is received within bore 58 of cap 56, and electric line 60 leading from IR source 46 is disposed within passage 62 in cap 56. Similarly, the combination of filter 50, detector 48, and board 52 with electric line 64 is received within hollowed portion 66 of cap 54.

Mounted on printed circuit board 52 are amplifier 68 for amplifying the detected infrared signal received from detector 48 and a voltage range control 70 for varying the signal strength of the amplified signal from amplifier 68 and a reference datum signal to be described below.

Continuing to refer to FIG. 4, infrared analyzer 26 further comprises microprocessor control system 72 connected between board 52 and infrared source 46. Microprocessor control system 72 comprises signal conditioner 74 which measures the voltage difference between received signals and then transmits a signal indicative of that energy differential to microprocessor controller 76. Microprocessor controller 76 performs several functions. One of the functions is to cause voltage range control 70 to emit a reference or datum voltage signal indicative of a non-radiating state of IR source 46. This datum signal is provided to signal conditioner 74 to be compared with a detected IR signal from detector 48. Microprocessor controller 76 can also cause voltage range control 70 to vary selectively the strength of the signals.

Controller 76 provides a timing signal to light timer 78, which in turn causes infrared source 46 to irradiate tube 42 and the lubricant passing therethrough. Controller 76 signals light timer 78 at a predetermined interval, such as every twelve seconds, thereby causing infrared source 46 to emit energy for one second every twelve seconds. Simultaneously with providing light timer 78 with a timing signal, a signal is relayed from light timer 78 to signal conditioner 74 indicating that a timing signal has been sent to infrared source 46. Upon receiving this signal from light timer 78, signal conditioner 74 measures the voltage difference between the first sequential pair of a detected infrared signal and datum signal. Signal conditioner 74 then provides an energy differential signal to controller 76 for determining the quality of the lubricant. Controller 76 is programmed to receive the measured voltage differential signal from signal conditioner 74 and to compute the quality level of the lubricant as a function of the voltage difference. Controller 76 then sends a signal to remote monitor 80 for visually displaying to an operator or observer the quality of the lubricant.

In operation, as lubricant flows through tube 42, infrared source 46 is pulsed on for one second and off for twelve seconds by controller 76 and light timer 78. The pulse of infrared energy passes through tube 42, the lubricant flowing therethrough, filter 50, and strikes detector 48. Detector 48 generates a voltage output signal in response to the amount of infrared energy falling on its surface. As indicated earlier, filter 50 can filter out all IR energy except that in a preferred range of about seven to fourteen microns or an optimum range of about 9.75 to 10.25 microns. Thus, the voltage output of the detected IR energy is a function of the amount of energy striking detector 48. Further, the amount of energy passing through tube 42 and the lubricant therein is controlled by the quality of the oil. As the contamination level increases in the lubricant, less infrared energy is passed through the lubricant due to absorption or scattering. In other words, as the amount or concentration of contaminants in the lubricant increase, less infrared energy transmits through the lubricant.

Generally, a mixture of clean lubricant and a small amount of refrigerant, such as 5% allows a maximum amount of infrared energy to pass therethrough, such that a one second burst of infrared energy can result in an output of one volt. This one volt output is the result of detector 48 sending a signal to amplifier 68, which amplifies the signal for voltage range control 70. As the lubricant degrades, more infrared energy is absorbed or scattered by the contaminants, and thus less infrared energy is detected by detector 48 such that the signal produced by amplifier 68 could result in a 0.6 volt output. Thus, the 0.4 voltage difference is due to absorption or scattering of infrared energy by the contaminated lubricant.

Voltage range control 70 sends the amplified detected signal to signal conditioner 74. After the one second burst of infrared energy, controller 76 causes voltage range control 70 to emit a voltage datum signal, such as 0.5 volts, to signal conditioner 74. Upon receipt of a timing signal from light timer 78, signal conditioner 74 will then measure the voltage difference between the first received amplified detected infrared signal and the next succeeding datum signal, and then send a voltage differential signal to controller 76. Controller 76 is programmed to compute the quality of oil as determined by the voltage differential of the two signals, and relays a signal to remote monitor 80. For example, when infrared energy is pulsed for one second, good lubricant will result in a one volt output which is a 0.5 voltage change relative to the 0.5 voltage datum signal. Severely contaminated lubricant can result in a 0.6 voltage output which is a 0.1 voltage difference when compared with the datum voltage. Controller 76 is programmed to correlate the oil quality with the voltage differential between the signals. Controller 76 can vary the datum voltage signal and amplifier 68 can be chosen to amplify a received signal to a desired output, thereby determining the voltage differential to be measured by signal conditioner 74.

The advantage of the differential voltage measurement as the useable signal is that the differential voltage is not affected by ambient temperature change. This eliminates the need for complex electronic circuitry for temperature compensation.

The present invention further contemplates infrared analyzer 26 being of more compact form, for example, it can be designed to be an inline sensor, thus eliminating the lines and connectors schematically illustrated in FIG. 2. Moreover, microprocessor control system 72 may be the control system that operates and controls the entire refrigeration, air conditioning, or similar system, wherein the computed oil quality is one of several signals, such as pressure, temperature, flow rate and like signals, received by the control system. Control system 72 further comprises a power supply and the necessary logic circuitry for its operation.

While this invention has been described as having a preferred embodiment, it will be understood that it is capable of further modifications. This application is therefore intended to cover any variations, uses, or adaptations of the invention following the general principles thereof, and including such departures from the present disclosure as come within known or customary practice in the art to which this invention pertains and fall within the limits of the appended claims.

What is claimed is:

1. An apparatus for infrared optical electronic qualitative analysis of a fluid independent of the temperature of the fluid, comprising:
   a passage means substantially transparent to infrared energy for delivering a flow of the fluid therethrough,
   an infrared means for radiating infrared energy through said passage means,
   a detection means including an infrared detector for detecting infrared energy radiated through said passage means, and a voltage controller for generating an infrared-responsive signal indicative of the detected infrared energy and a datum signal indicative of a non-radiating energy state of said infrared means, and
   a microprocessor control means for receiving and measuring an energy difference between said infrared-responsive and said datum signals, and for computing from the energy differential the quality of the fluid independent of the temperature thereof.

2. The apparatus of claim 1 wherein said microprocessor control means includes a light timer means for generating at a predetermined interval a timing signal to said infrared means, and said infrared means radiates infrared energy in response to the received said timing signal.

3. The apparatus of claim 1 wherein said microprocessor control means further includes a signal conditioning means for measuring the energy difference between said infrared-responsive and said datum signals in response to receiving said timing signal.

4. The apparatus of claim 1 wherein said infrared means radiates infrared energy in a predetermined bandwidth.

5. The apparatus of claim 1 wherein said detection means detects infrared energy in a predetermined bandwidth.

6. The apparatus of claim 1 further comprising a filter means disposed between said passage means and said detection means for permitting a selected bandwidth of infrared energy to be received by said detection means.

7. The apparatus of claim 1 further comprising a signal strength control means between said detection means and said microprocessor control means for selectively varying the strength of said infrared-responsive and said datum signals.

8. The apparatus of claim 1 further comprising a remote monitor means connected to said microprocessor control means for visually indicating the computed quality of the fluid.

9. In a refrigeration, air conditioning, or similar system including a condenser, an evaporator, a compressor, and a lubrication system for delivering a lubricant to said compressor, an apparatus for determining the quality of the lubricant, comprising:

a lubricant delivery means in said lubrication system for delivering a flow of lubricant, an infrared means for radiating infrared energy through said lubricant delivery means, an infrared detection means including an infrared detector for detecting infrared energy radiated through said lubricant delivery means, and a voltage controller for generating a first signal indicative of the detected infrared energy and a second signal indicative of a non-radiating state of said infrared means, and a microprocessor control means for receiving and measuring a difference between said first and said second signals, and for computing from said difference a quality level of the lubricant independent of the temperature thereof, and for generating a third signal indicative of the computed quality level, and a monitor means for receiving said third signal and visually displaying the computed lubricant quality.

10. The system of claim 9 wherein said lubricant delivery means is made of a material substantially transparent to the received infrared energy.

11. The system of claim 9 wherein said infrared means radiates infrared energy in a range of about seven to fourteen microns.

12. The system of claim 9 wherein said infrared detection means detects infrared energy in a range of about seven to fourteen microns.

13. The system of claim 9 wherein said microprocessor control means includes a light timer means for generating at a predetermined interval a timing signal to said infrared means, and said infrared means radiates infrared energy in response to the received said timing signal.

14. The system of claim 9 wherein said microprocessor control means further includes a signal conditioning means for measuring the energy difference between said first and said second signals in response to the received said timing signal.

15. The system of claim 9 further comprising a filter means disposed between said lubricant delivery means and said infrared detection means for permitting passage therethrough of infrared energy only within a range of about seven to fourteen microns.

16. The system of claim 9 further comprising a signal strength control means for selectively varying the strength of said first and said second signals.

17. A method for infrared optical electronic qualitative analysis of a fluid independent of the temperature of the fluid, comprising the steps of:

providing fluid to be analyzed, radiating infrared energy through the fluid, detecting the infrared energy radiated through the fluid, generating an infrared responsive signal indicative of the detected infrared energy, generating a datum signal indicative of a non-radiating infrared energy state, determining the energy difference between the infrared-responsive and the datum signals, and computing from the determined energy difference the quality of the fluid independent of the temperature thereof.

18. The method of claim 17 wherein the infrared energy radiated is within a predetermined bandwidth.

19. The method of claim 17 wherein the infrared energy detected is within a predetermined bandwidth.

20. The method of claim 17 further comprising the step of generating at a predetermined interval a timing signal in response to which infrared energy is radiated.

21. The method of claim 17 further comprising the step of selectively varying the strength of the infrared responsive signal and the datum signal.

22. The method of claim 17 further comprising the step of visually indicating the computed fluid quality.

* * * * *